United States Patent
Panda et al.

(10) Patent No.: US 7,256,399 B2
(45) Date of Patent: Aug. 14, 2007

(54) NON-DESTRUCTIVE IN-SITU ELEMENTAL PROFILING

(75) Inventors: Siddhartha Panda, Beacon, NY (US); Michael R. Sievers, Poughkeepsie, NY (US); Richard S. Wise, New Windsor, NY (US)

(73) Assignee: International Business Machines Corporation, Armonk, NY (US)

( * ) Notice: Subject to any disclaimer, the term of this patent is extended or adjusted under 35 U.S.C. 154(b) by 212 days.

(21) Appl. No.: 10/907,591

(22) Filed: Apr. 7, 2005

(65) Prior Publication Data

US 2006/0227321 A1    Oct. 12, 2006

(51) Int. Cl.
    *G01N 23/227*    (2006.01)
(52) U.S. Cl. .................. 250/305; 250/307; 438/5; 438/10
(58) Field of Classification Search .............. None
    See application file for complete search history.

(56) References Cited

U.S. PATENT DOCUMENTS

| | | | |
|---|---|---|---|
| 4,902,631 A * | 2/1990 | Downey et al. ............... | 438/10 |
| 5,434,422 A | 7/1995 | Iwamoto et al. | |
| 5,635,836 A | 6/1997 | Kirtley et al. | |
| 5,922,179 A | 7/1999 | Mitro et al. | |
| 6,259,092 B1 | 7/2001 | Brizzolara et al. | |
| 6,365,905 B1 | 4/2002 | Koyama et al. | |
| 6,407,850 B1 | 6/2002 | Rojo et al. | |
| 6,545,272 B1 * | 4/2003 | Kondo ........................ | 250/305 |
| 6,782,072 B2 | 8/2004 | Lin | |
| 2002/0005492 A1 | 1/2002 | Hashikawa et al. | |
| 2002/0050565 A1 | 5/2002 | Tokuda et al. | |
| 2003/0080292 A1* | 5/2003 | Watson et al. ............... | 250/306 |
| 2004/0060904 A1 | 4/2004 | Herschbein et al. | |
| 2004/0112857 A1 | 6/2004 | Herschbein et al. | |

(Continued)

FOREIGN PATENT DOCUMENTS

EP    4031676 A1    4/1992

(Continued)

OTHER PUBLICATIONS

Students abstracts: LBNL-Materials Sciences, "Student Abstracts: Materials Sciences at LBNL", http://www.scied-science.doe.gov/scied/Abstracts2003/LBNLms.htm, 2 pages.

(Continued)

*Primary Examiner*—Jack I. Berman
(74) *Attorney, Agent, or Firm*—Lisa U. Jaklitsch; Hoffman, Warnick & D'Alessandro LLC

(57) ABSTRACT

A non-destructive in-situ elemental profiling of a layer in a set of layers method and system are disclosed. In one embodiment, a first emission of a plurality of photoelectrons is caused from the layer to be elementally profiled. An elemental profile of the layer is determined based on the emission. In another embodiment, a second emission of a plurality of photoelectrons is also received from the layer, and an elemental profile is determined by comparison of the resulting signals. A process that is altering the layer can then be controlled "on-the-fly" to obtain a desired material composition. Since the method can be employed in-situ and is non-destructive, it reduces turn around time and lowers wafer consumption. The invention also records the composition of all processed wafers, hence, removing the conventional statistical sampling problem.

18 Claims, 1 Drawing Sheet

U.S. PATENT DOCUMENTS

2004/0129879 A1     7/2004    Furiki et al.
2004/0132287 A1     7/2004    Fischer et al.

FOREIGN PATENT DOCUMENTS

JP            2000030658       1/2000

OTHER PUBLICATIONS

Training Courses 2004, FEI Company, Scanning Electron Microscopy, Small Dualbeam and Applications, 17 Pages.

SEM Substages and SPM Accessories from Ernest R. Fullam, Inc., 7 pages, http:www.fullam.com/Sem_subs.htm, "SEM SUBSTAGES". http://ist-socrates.berkeley.edu/~es196/projects/2000final/mussa.pdf 12 pages http://ist-socrates.berkeley.edu/~es196/projects/2000final/mussa.pdf 12 pages.

http://ist-socrates.berkeley.edu/~es196/projects/2000final/ 2 pages.

* cited by examiner

NON-DESTRUCTIVE IN-SITU ELEMENTAL PROFILING

This application is related to co-pending U.S. Ser. No. 10/904,883, entitled "Endpoint Detection for the Patterning of Layered Materials," filed Dec. 2, 2004, which is hereby incorporated by reference.

BACKGROUND OF THE INVENTION

1. Technical Field

The present invention relates generally to composition determination techniques, and more particularly, to non-destructive, in-situ elemental profiling.

2. Related Art

Conventionally, determination of a composition or elemental profiling of a film, for example, in the semiconductor industry, requires testing in a location out of the manufacturing environment. Unfortunately, removal of a product from the manufacturing environment creates a number of disadvantages. First, any removal of a product from the manufacturing process increases processing time. Second, it prohibits "on-the-fly" adjustments to process conditions, e.g., gas flow rates, annealing temperature, pressure, etc. Third, conventional testing is dependent on statistical sampling because the product tested is assumed to have the properties of the lot from which it is taken.

Another shortcoming of conventional elemental profiling techniques is that they are destructive to the test product. For example, two common techniques are secondary ion mass spectroscopy (SIMS) elemental profiling and auger elemental profiling. Both of these techniques, however, are destructive techniques. Moreover, each must be conducted ex-situ of the manufacturing process.

These and other deficiencies in the prior art are overcome through the invention.

In view of the foregoing, there is a need in the art for a non-destructive in-situ elemental profiling that does not suffer from the problems of the related art.

SUMMARY OF THE INVENTION

The invention includes a non-destructive in-situ elemental profiling of a layer in a set of layers method and system. In one embodiment, a first emission of a plurality of photoelectrons is caused from the layer to be elementally profiled. An elemental profile of the layer is determined based on the emission. In another embodiment, a second emission of a plurality of photoelectrons is also received from the layer, and an elemental profile is determined by comparison of the resulting signals. A process that is altering the layer can then be controlled "on-the-fly" to obtain a desired material composition. Since the method can be employed in-situ and is non-destructive, it reduces turn around time and lowers wafer consumption. The invention also records the composition of all processed wafers, hence, removing the conventional statistical sampling problem.

A first aspect of the invention is directed to a method of elemental profiling a layer in a set of layers undergoing a process, the method comprising the steps of: irradiating the layer with a plurality of photons; receiving an emission of a plurality of photoelectrons from the layer; and determining an elemental profile of the layer based on the emission.

A second aspect of the invention includes a method of elemental profiling a layer undergoing a process, the method comprising the steps of: receiving an emission of a plurality of photoelectrons from the layer; and determining an elemental profile of the layer based on the emission.

A third aspect of the invention related to a system for elemental profiling a thickness of a layer in a set of layers undergoing a process, the system comprising: a causation device for causing an emission of a plurality of photoelectrons from the layer in the set of layers; and at least two detection devices for determining the elemental profile of the layer based on one of a receipt of the emission and an absence of the emission.

The foregoing and other features of the invention will be apparent from the following more particular description of embodiments of the invention.

BRIEF DESCRIPTION OF THE DRAWINGS

The embodiments of this invention will be described in detail, with reference to the following figure wherein.

DETAILED DESCRIPTION

Figure 1:
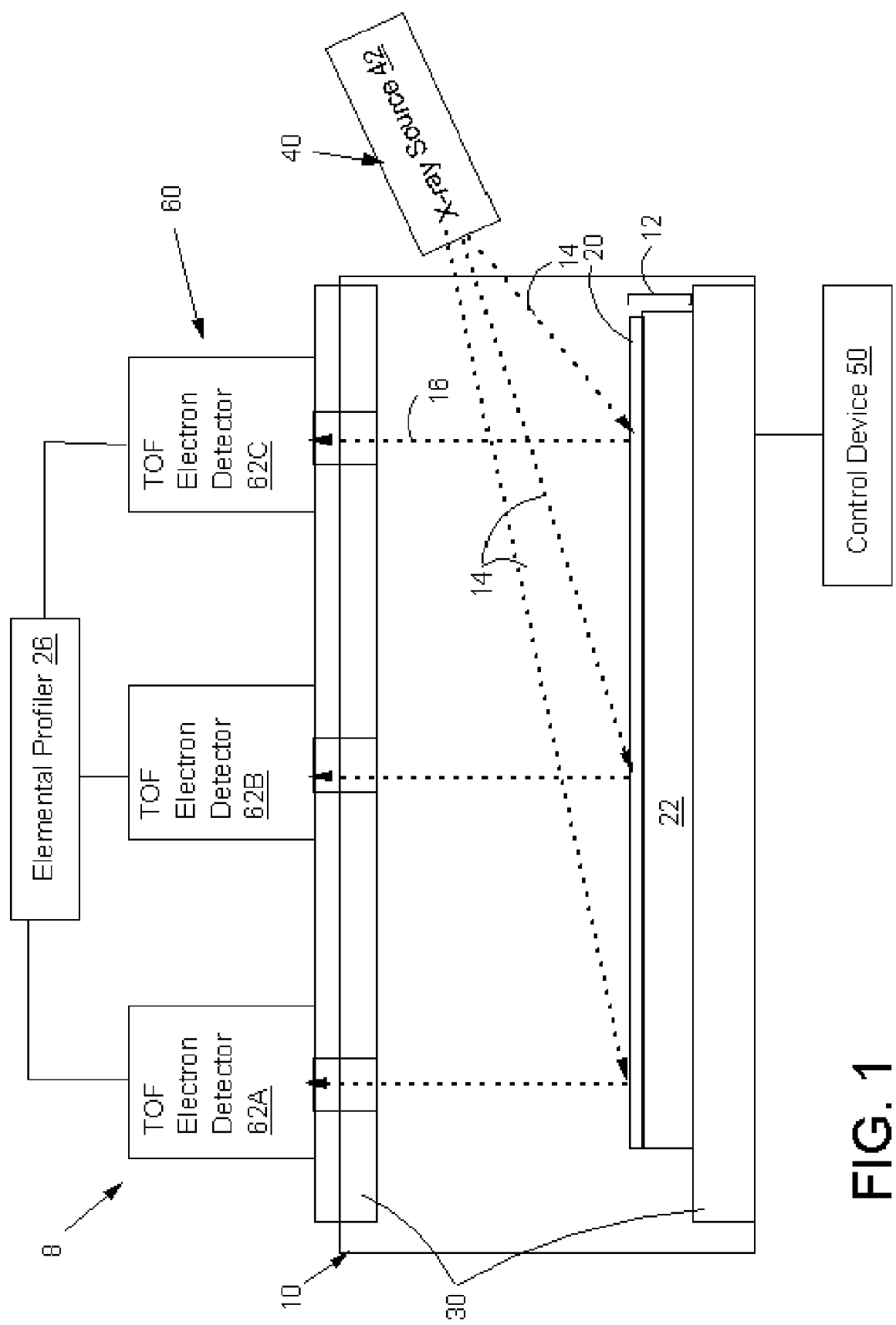
FIG. 1 shows elemental profiling according to the invention.

With reference to the accompanying drawing, FIG. 1 illustrates an elemental profiling system 8 according to the invention. As shown in FIG. 1, the invention determines an elemental profile, e.g., of a composition, of a layer in a set of layers undergoing a process in situ of a process chamber 10. In accordance with the invention, a layered material 12 including a topmost layer 20, e.g., a semiconductor, dielectric, or conductor of a semiconductor wafer, is irradiated with an x-ray beam 14, which comprises a plurality of photons, and a photoelectron emission 16 is caused in response to this irradiation. Photoelectron emissions 16 have signals with energy levels unique to the material of layer 20 from which the photoelectrons are emitted. The material can be a compound or an element, but the material of layer 20 and a set of layers (layered material 12) thereabout (under, adjacent or over) differ only in stoichiometry. Because photoelectrons have a short mean free path, photoelectrons generated from materials greater than approximately 9 nm below the surface are not detectable. Such photoelectrons are collisionally de-energized. Based on photoelectron emission 16, an elemental profile can be determined by an elemental profiler 26 for topmost layer 20.

As shown in FIG. 1, the details of elemental profiling system 8 will now be described. Layered material 12 rests within process chamber 10 during processing. Process chamber 10 includes or is coupled to an alteration device 30 and a causation device 40. Alteration device 30 includes, but is not limited to, a material removal or deposition tool. A material removal tool includes, but is not limited to, a plasma etch or reactive ion etch (RIE) tool. A deposition tool includes any now known or later developed material deposition tools, e.g., a chemical vapor deposition tool. Alteration device 30 is controlled by control device 50. Causation device 40 causes emission of photoelectrons 16, e.g., by exposing layered material 12 to x-ray beam (photons) 14. Causation device 40 includes, but is not limited to, a standard x-ray photoelectron spectrometer (XPS) 42. A detection device 60 includes at least two photoelectron detectors, such as but not limited to, time of flight (TOF) photoelectron detectors 62A, 62B, 62C. Elemental profiler 26 includes any computational hardware or software required to convert signals from detection device 60 into an elemental profile.

By way of overview, layered material 12 in the form of a polysilicon stack undergoing an etch ("PC etch") process will be described in accordance with the method of the invention. At the time of PC etch, a semiconductor wafer has approximately 2000 Å of patterned photoresist, approximately 1000 Å to approximately 1500 Å of underlying polysilicon, and approximately 10 Å to approximately 26 Å of further underlying gate oxide. X-ray beam (photon) exposure 14 irradiates the surface of the wafer. Detection device 60 detects a photoelectron emission 16 from the photoresist and polysilicon, and converts it to a signal, but does not detect the photoelectron emission (signal) from the gate oxide, which underlies the photoresist and polysilicon. Therefore, the photoelectron emission (signal) from the gate oxide is undetectable because of the thickness of the photoresist and polysilicon layers above the gate oxide. As the polysilicon is etched, the thickness of the polysilicon decreases. Once the thickness is less than or equal to approximately 9.0 nm, photoelectrons generated from the gate oxide are detectable. Accordingly, at such time a photoelectron emission unique to the gate oxide, such as oxygen, is detectable. A constant photoelectron emission 16 signal of oxygen from the photoresist remains; however, that signal becomes a background signal to the photoelectron emission signal of the gate oxide. Accordingly, upon evaluation of photoelectron emission 16 (and perhaps comparison of substantially different signals from a topmost layer 20 and an underlying layer), an elemental profile can be determined by elemental profiler 26 for topmost layer 20.

Control of the process in-situ based on the elemental profile can then occur via control device 50 and may include, for example, adjusting a gas flow rate, a chamber temperature, an annealing temperature, a pressure, etc. It should be recognized that the teachings of the invention also work in terms of deposition of material. In this case, as a material is being deposited on layered material 12, the photoelectron emission changes according to the amount of material being deposited and the chemical makeup of topmost layer 20.

The invention allows in-situ monitoring of a surface chemical composition during processing (e.g., etching or deposition) and is able to adjust the process variables "on-the-fly" to obtain a desired material composition and/or layer depth. The invention reduces turn around time because it is in-situ, and lowers wafer consumption because it is non-destructive. The invention also records the composition of all processed wafers, hence, removing the conventional statistical sampling problem.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A method of elemental profiling a layer in a set of layers undergoing a process, the method comprising:
   irradiating the layer with a plurality of photons;
   receiving an emission of a plurality of photoelectrons from the layer;
   determining an elemental profile of the layer based on the emission; and
   controlling the process in-situ based on the elemental profile, including adjusting at least one of: a gas flow rate, a chamber temperature, an annealing temperature, or a pressure.

2. The method of claim 1, wherein the emission has a signal unique to a material of the layer undergoing thickness alteration and another emission of a plurality of photoelectrons from the layer has a signal unique to a material of an underlying layer.

3. The method of claim 2, wherein the detecting step farther comprises comparing the signals.

4. The method of claim 1, wherein the material of the layer includes one of an element and a compound and the set of layers comprises one of a semiconductor, a dielectric, and a conductor.

5. The method of claim 1, wherein a material of the layer undergoing thickness alteration and a material of an underlying layer differ only in stoichiometry.

6. A method of elemental profiling a layer undergoing a process, the method comprising:
   receiving an emission of a plurality of photoelectrons from the layer;
   determining an elemental profile of the layer based on the emission; and
   controlling the process in-situ based on the elemental profile, including adjusting at least one of: a gas flow rate, a chamber temperature, an annealing temperature, or a pressure.

7. The method of claim 6, further comprising the step of causing the emission of the plurality of photoelectrons.

8. The method of claim 7, wherein the causing step includes irradiating the layer with a plurality of photons.

9. The method of claim 6, wherein the process includes one of depositing a material on the layer and removing a material from the layer.

10. The method of claim 6, wherein the layer includes at least one of a semiconductor, a dielectric, and a conductor.

11. The method of claim 6, wherein the emission has a signal unique to a material of the layer.

12. The method of claim 11, wherein the material includes one of an element and a compound.

13. The method of claim 11, wherein the material of the layer and a set of layers thereabout differ only in stoichiometry.

14. A system for elemental profiling a thickness of a layer in a set of layers undergoing a process, the system comprising:
   a process chamber containing the layer in the set of layers undergoing the process in situ;
   a causation device for causing an emission of a plurality of photoelectrons from the layer in the set of layers;
   an alteration device for altering the process in situ; and
   at least two detection devices for determining the elemental profile of the layer based on one of a receipt of the emission and an absence of the emission.

15. The system of claim 14, further comprising a control device for controlling the alteration device altering the process based on the elemental profile.

16. The system of claim 15, wherein the control device adjusts at least one of: a gas flow rate, a chamber temperature, an annealing temperature or a pressure.

17. The system of claim 14, wherein the causation device includes an x-ray photoelectron spectrometer.

18. The system of claim 14, wherein each detection device includes a time of flight photoelectron detector.

* * * * *